(12) United States Patent
Arnin et al.

(10) Patent No.: US 8,486,145 B2
(45) Date of Patent: Jul. 16, 2013

(54) FLEXURE LIMITER FOR SPINAL PROSTHESIS

(75) Inventors: Uri Arnin, Kiryat Tivon (IL); Yuri Sudin, Lod (IL)

(73) Assignee: Premia Spine Ltd., Ramat Poleg, Netanya (IL)

( * ) Notice: Subject to any disclaimer, the term of this patent is extended or adjusted under 35 U.S.C. 154(b) by 90 days.

(21) Appl. No.: 11/228,245

(22) Filed: Sep. 19, 2005

(65) Prior Publication Data

US 2007/0083264 A1    Apr. 12, 2007

(51) Int. Cl.
*A61F 2/44*        (2006.01)
(52) U.S. Cl.
USPC ........................................................ 623/17.15
(58) Field of Classification Search
USPC ..................... 623/17.11–17.16; 606/247–249
See application file for complete search history.

(56) References Cited

U.S. PATENT DOCUMENTS

| | | | | |
|---|---|---|---|---|
| 4,759,766 A | * | 7/1988 | Buettner-Janz et al. | 623/17.15 |
| 4,759,769 A | * | 7/1988 | Hedman et al. | 623/17.13 |
| 5,401,269 A | * | 3/1995 | Buttner-Janz et al. | 623/17.15 |
| 5,683,465 A | * | 11/1997 | Shinn et al. | 623/17.14 |
| 5,893,889 A | * | 4/1999 | Harrington | 623/17.16 |
| 5,895,428 A | | 4/1999 | Berry | |
| 6,395,032 B1 | * | 5/2002 | Gauchet | 623/17.12 |
| 6,440,169 B1 | * | 8/2002 | Elberg et al. | 623/17.16 |
| 6,692,495 B1 | * | 2/2004 | Zacouto | 606/247 |
| 7,060,097 B2 | * | 6/2006 | Fraser et al. | 623/17.11 |
| 2002/0128715 A1 | * | 9/2002 | Bryan et al. | 623/17.15 |
| 2003/0045939 A1 | * | 3/2003 | Casutt | 623/17.15 |
| 2003/0045940 A1 | * | 3/2003 | Eberlein et al. | 623/17.16 |
| 2003/0135277 A1 | * | 7/2003 | Bryan et al. | 623/17.12 |
| 2003/0176923 A1 | * | 9/2003 | Keller et al. | 623/17.14 |
| 2004/0093082 A1 | | 5/2004 | Ferree | |
| 2004/0243238 A1 | | 12/2004 | Arnin et al. | |
| 2004/0243240 A1 | * | 12/2004 | Beaurain et al. | 623/17.14 |
| 2005/0165486 A1 | * | 7/2005 | Trieu | 623/17.13 |
| 2005/0187631 A1 | * | 8/2005 | Van Hoeck et al. | 623/17.13 |
| 2005/0197705 A1 | * | 9/2005 | Arnin et al. | 623/17.15 |
| 2006/0129239 A1 | * | 6/2006 | Kwak | 623/17.13 |
| 2006/0293752 A1 | * | 12/2006 | Moumene et al. | 623/17.13 |

FOREIGN PATENT DOCUMENTS

WO        2005044152        5/2005

* cited by examiner

*Primary Examiner* — Mary Hoffman
(74) *Attorney, Agent, or Firm* — Dekel Patent Ltd.; David Klein

(57) ABSTRACT

Apparatus including a first spinal prosthetic member that may articulate with a second spinal prosthetic member, the first and second spinal prosthetic members flexing relative to one another about a lateral-medial axis corresponding to a lateral-medial axis of a body, and a flexure limiting member attached to the first and second spinal prosthetic members that limits flexure about the lateral-medial axis.

15 Claims, 5 Drawing Sheets

FLEXURE LIMITER FOR SPINAL PROSTHESIS

FIELD OF THE INVENTION

The present invention is generally related to apparatus and methods for spinal prostheses, and particularly to apparatus and methods for limitation of flexure of a spinal prosthesis.

BACKGROUND OF THE INVENTION

Through disease or injury, the laminae, spinous process, or articular processes of one or more vertebral bodies can become damaged, such that the vertebrae no longer articulate or properly align with each other. This can result in an undesired anatomy, loss of mobility, and pain or discomfort. For example, spinal stenosis, as well as spondylosis, spondylolisthesis, and other degenerative phenomena may cause back pain, especially lower back pain, such as in the lumbosacral (L4-S1) region. Such phenomena may be caused by a narrowing of the spinal canal by a variety of causes that result in the pinching of the spinal cord and/or nerves in the spine.

The prior art has many spinal prostheses designed to help the patient with various back problems. For example, published PCT Patent Application WO 2005/044152, assigned to the present assignee, describes a spinal prosthesis having a unitary body with three or more attachment points attachable to spinal structure. The unitary body includes a flexure assembly positioned between first and second attachment members, wherein flexure of the flexure assembly permits movement of the first attachment member relative to the second attachment member. The flexure assembly may be adapted to flex omnidirectionally. A plurality of pedicle screws (e.g., polyaxial pedicle screws with polyaxial swivel heads) may be attached to or integrally formed with the spinal prosthesis.

SUMMARY OF THE INVENTION

The present invention seeks to provide apparatus and methods for limitation of flexure of a spinal prosthesis, as is described more in detail hereinbelow. The prostheses disclosed herein are particularly advantageous for the posterior portion of the spine, but the invention is not limited to the posterior portion of the spine.

There is thus provided in accordance with an embodiment of the present invention apparatus including a first spinal prosthetic member that may articulate with a second spinal prosthetic member, the first and second spinal prosthetic members flexing relative to one another about a lateral-medial axis corresponding to a lateral-medial axis of a body, and a flexure limiting member attached to the first and second spinal prosthetic members that limits flexure about the lateral-medial axis.

The apparatus can include one or more of the following features. For example, the first spinal prosthetic member may include a first attachment member and a first articulating member that extends therefrom, and the second spinal prosthetic member may include a second attachment member and a second articulating member that extends therefrom, the first articulating member articulating with the second articulating member and the first and second attachment members being attachable to spinal structure. The flexure limiting member may be attached to a non-peripheral or peripheral portion of the first and second attachment members.

The flexure limiting member may include one or more slim elongate members. The flexure limiting member may be preshaped with one or more bends. For example, the flexure limiting member may have at least one first curved portion and a second curved portion, curved opposite to the at least one first curved portion and joined thereto at an inflection point. The flexure limiting member may include attachment elements at ends thereof for attachment to the first and second attachment members.

DETAILED DESCRIPTION OF EMBODIMENTS

Figure 1:
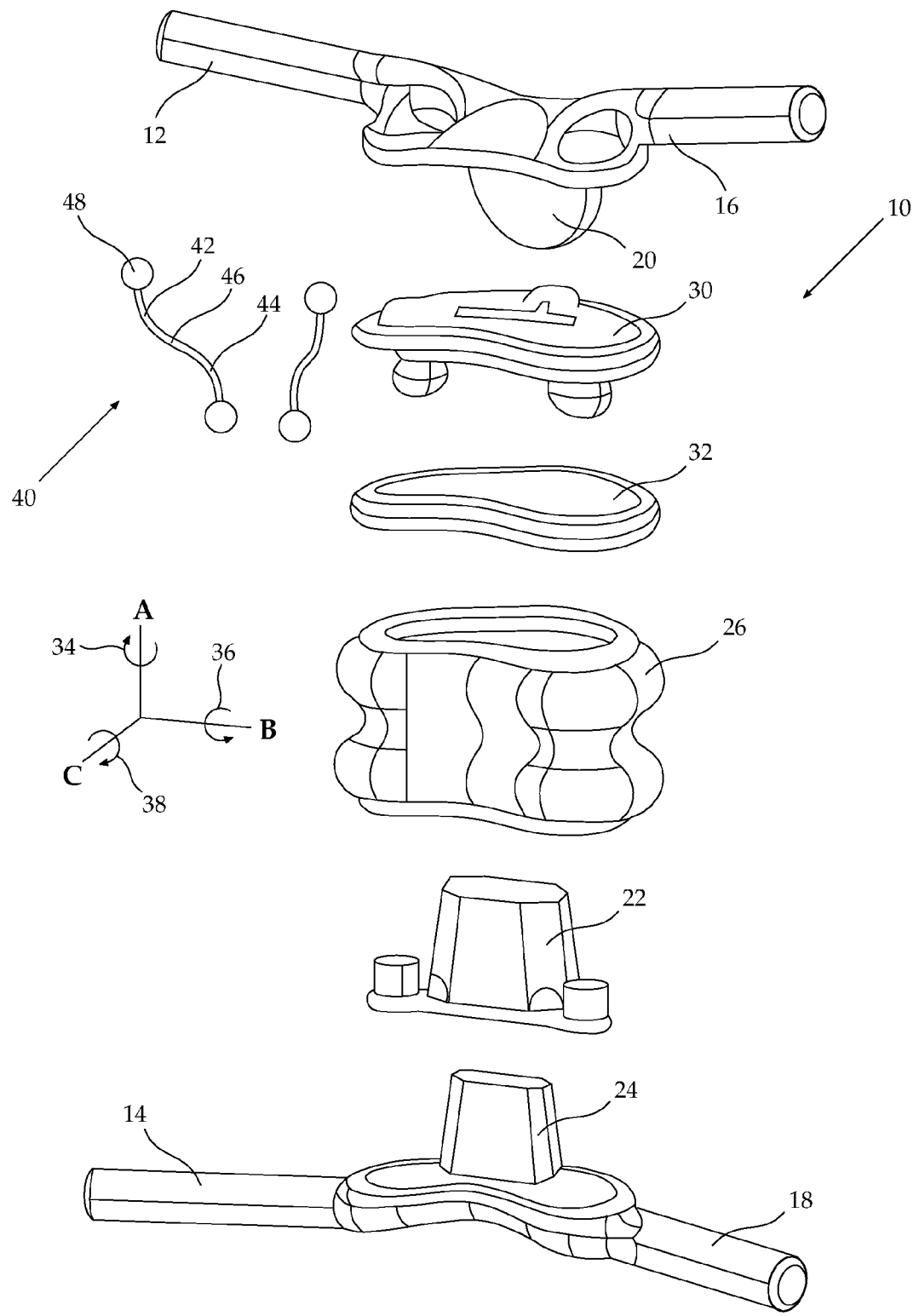
FIG. 1 is a simplified exploded illustration of a spinal prosthesis that includes a flexure limiting member, constructed and operative in accordance with an embodiment of the present invention.
Figure 2A:
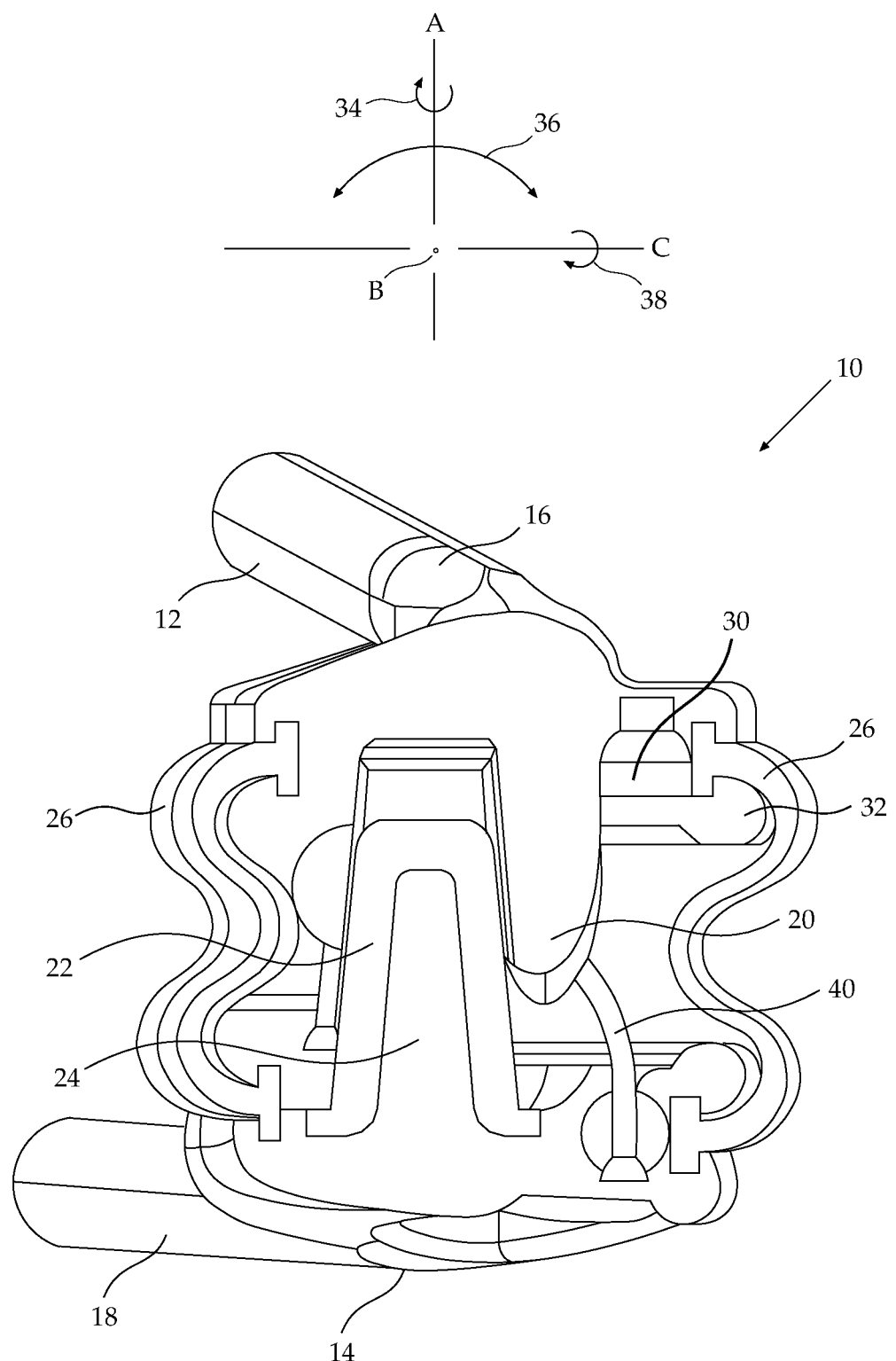
FIGS. 2A and 2B are simplified sectional illustrations of the spinal prosthesis of FIG. 1, showing the internal attachment of the flexure limiting member, in accordance with an embodiment of the present invention.
Figure 2B:
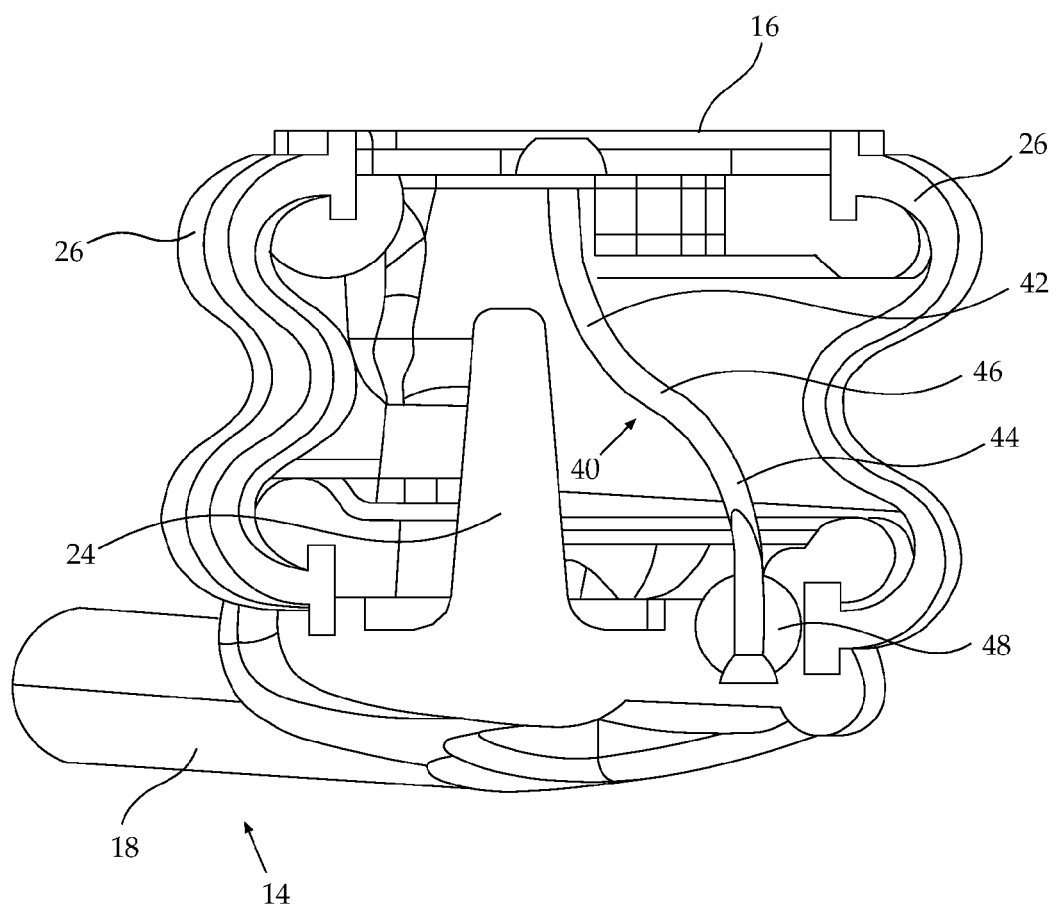

Reference is now made to FIGS. 1, 2A and 2B, which illustrate a spinal prosthesis 10, constructed and operative in accordance with an embodiment of the present invention.

The spinal prosthesis 10 may include a first spinal prosthetic member 12, which may be attached to a first spinal structure, such as but not limited to, a vertebra (e.g., L3, not shown). The spinal prosthesis 10 may also include a second spinal prosthetic member 14, which may be attached to a second spinal structure, such as but not limited to, a vertebra (e.g., L4, not shown).

In the non-limiting illustrated embodiment, the first spinal prosthetic member 12 may include a first (e.g., upper or superior) attachment member 16 and the second spinal prosthetic member 14 may include a second (e.g., lower or inferior) attachment member 18. The first and second attachment members 16 and 18 may be rigid or non-rigid, formed of materials including, but not limited to, a biocompatible material such as a metal, e.g., stainless steel, titanium or titanium alloy, cobalt chromium alloys, plastics or other hard, rigid materials or any combination of the above. The attachment members 16 and 18 may include, without limitation, a generally flat plate with rounded prongs that extend outwards therefrom. Pedicle screws (not shown) may be used to attach the rounded prongs to spinal structure, such as but not limited to, the pedicles or spinous processes.

The first and second spinal prosthetic members 12 and 16 may articulate with each other to form an articulating assembly. For example, the first spinal prosthetic member 12 may include a first articulating member 20 that extends downward (in the sense of the drawings) from the flat plate of attachment member 16. First articulating member 20 articulates with (e.g., glides over) a second articulating member 22 that may fit over a protrusion 24 that extends upward (in the sense of the drawings) from the flat plate of attachment member 18. (Protrusion 24 may be rigid and made of the same material as attachment member 18.) A boot 26 may optionally be placed at least partially or fully around the first and second articulating members 20 and 22. (Boot 26 is shown cut in FIGS. 2A and 2B.) The boot 26 may have any suitable shape or size, such as but not limited to, a ring, a stocking, an ellipsoid and other shapes. First and second articulating members 20 and 22, as well as boot 26, may be constructed of compliant, elastomeric materials including, but not limited to, polyurethane containing materials, silicone containing materials, polyethylene based elastomers, hydrogels, and polypropylene containing materials. Boot 26 may optionally be made of cloth (woven or non-woven synthetic or natural fibers). One or more fixation plates 30 and 32 may be used to assemble boot 26 with either one or both of attachment members 16 and 18. The parts may be assembled together, without limitation, such as with screws (not shown) that pass through mounting holes.

First articulating member 20 may articulate with second articulating member 22 omnidirectionally. For example, the articulating members 20 and 22 may permit rotation about three mutually orthogonal axes, the vertical axis labeled axis A, the lateral-medial axis labeled axis B (corresponding to the side-to-side axis of a body) and the anterior-posterior axis labeled axis C (corresponding to the front-to-rear axis of the body). For example, first and second articulating members 20 and 22 may flex relative to each other angularly in the direction of an arrow 34 about axis A, angularly in the direction of an arrow 36 about axis B and angularly in the direction of an arrow 38 about axis C.

In accordance with an embodiment of the present invention, a flexure limiting member 40 may be provided that limits the angular flexure of first and second articulating members 20 and 22 relative to each other about axis B, i.e., the lateral-medial axis. "Limiting" the flexure throughout the specification and claims refers to diminishing the angular distance and/or the angular velocity the articulating members can move relative to one another if they were free to articulate with no restraint. Flexure limiting member 40 may be attached to first and second attachment members 16 and 18. Flexure limiting member 40 may be attached to a non-peripheral portion of first and second attachment members 16 and 18 (as opposed to boot 26 which is attached to the periphery of first and second attachment members 16 and 18).

Flexure limiting member 40 may be constructed, without limitation, from a medically safe plastic, such as polyurethane or polyetheretherketone, the latter commercially available as brand name PEEK from Victrex of England.

For example, as seen in the embodiment of FIGS. 1, 2A and 2B, flexure limiting member 40 may include one or more slim elongate members, such as but not limited to, cables, rods, bars, wires and the like. (For the sake of clarity, FIG. 2B does not show most of first attachment member 16.) Flexure limiting member 40 may be pre-shaped with one or more bends. For example, as shown in the non-limiting embodiment, flexure limiting member 40 has a first curved portion 42 and a second curved portion 44, curved opposite to the first curved portion 42 and joined thereto at an inflection point 46. ("Inflection point" is the point where the curvature changes from concave to convex or vice versa.) Flexure limiting member 40 may include attachment elements 48 at ends thereof for attachment to first and second attachment members 16 and 18. For example, attachment elements 48 may be bulbous ends of flexure limiting member 40 that snap through mounting holes or are fixed in place by fixation plates 30 or 32.

Figure 3:
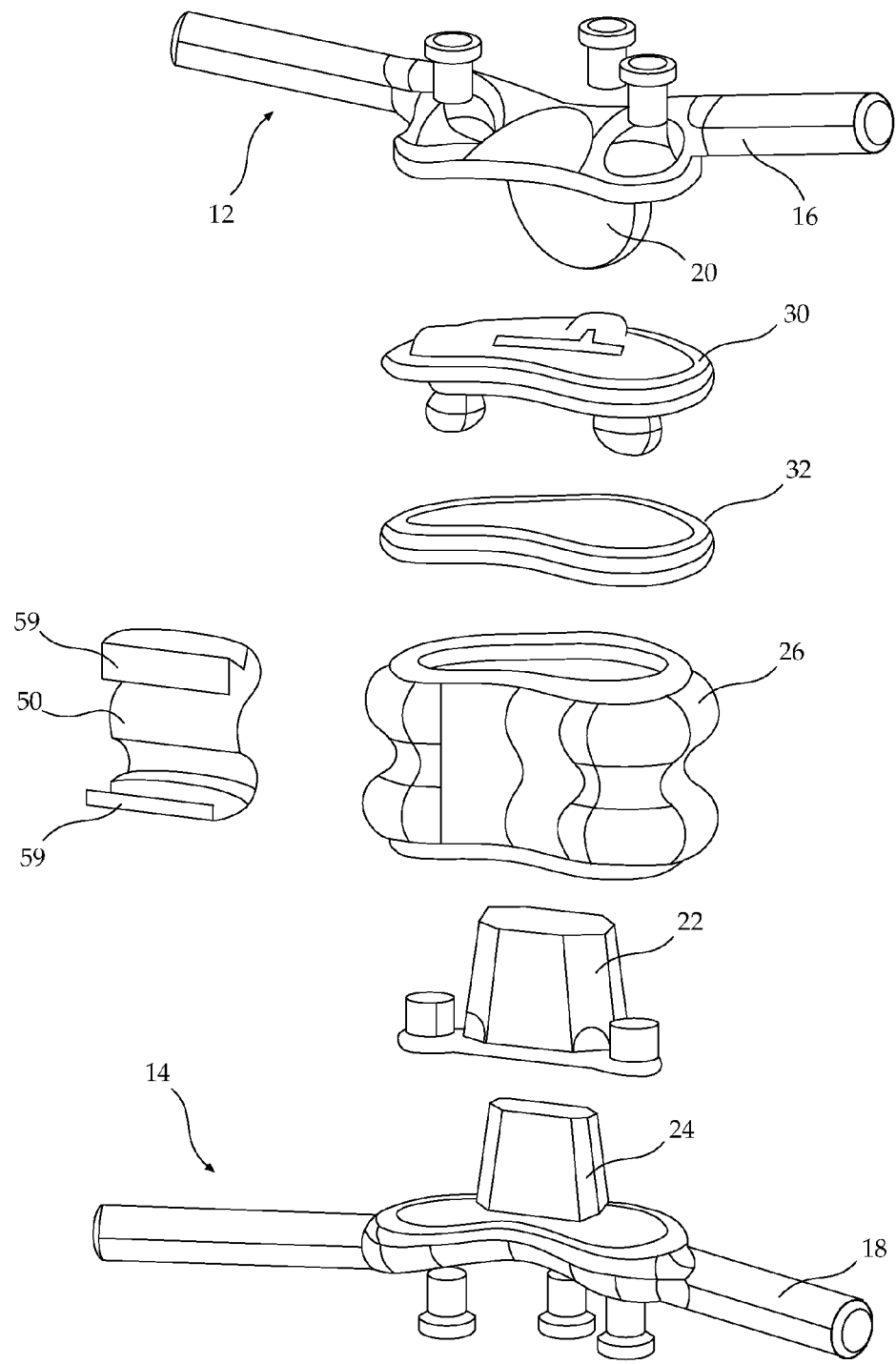
FIG. 3 is a simplified exploded illustration of a spinal prosthesis that includes a flexure limiting member, constructed and operative in accordance with another embodiment of the present invention.
Figure 4:
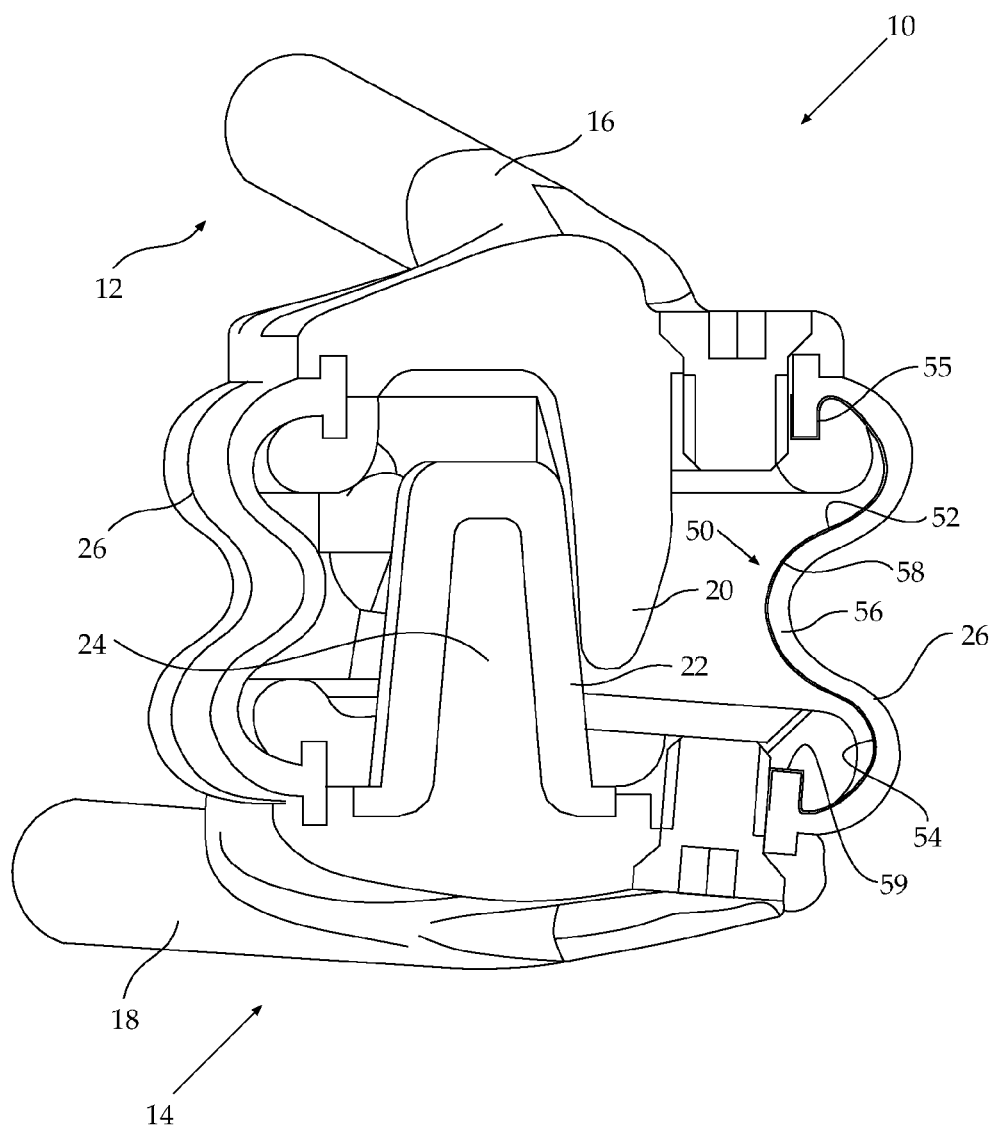
FIG. 4 is a simplified sectional illustration of the spinal prosthesis of FIG. 3, showing the internal attachment of the flexure limiting member, in accordance with an embodiment of the present invention.

Reference is now made to FIGS. 3 and 4, which illustrate spinal prosthesis 10, constructed and operative in accordance with another embodiment of the present invention. In this embodiment, spinal prosthesis 10 includes a flexure limiting member 50 attached to a peripheral portion of first and second attachment members 16 and 18 (inwards of the optional boot 26). Without limitation, flexure limiting member 50 may be in the form of an at least partial or full boot, or in the shape of a relatively wide ribbon.

Flexure limiting member 50 may be pre-shaped with one or more bends. For example, as shown in the non-limiting embodiment, flexure limiting member 50 has a first curved portion 52, a second curved portion 54, both curved in the same direction, and a third curved portion 56 curved opposite to the first and second curved portions 52 and 54. The curved portions are joined to each other at inflection points 58. Flexure limiting member 50 may include attachment elements 59 at ends thereof for attachment to first and second attachment members 16 and 18. For example, attachment elements 59 may be flanges that are fixedly received in grooves 55 formed in first and second attachment members 16 and 18.

Although the invention has been described in conjunction with specific embodiments thereof, many alternatives, modifications and variations are apparent to those skilled in the art. Accordingly, all such alternatives, modifications and variations fall within the spirit and scope of the following claims.

What is claimed is:

1. Apparatus comprising:
a first spinal prosthetic member that flexes relative to a second spinal prosthetic member about a lateral-medial axis corresponding to a lateral-medial axis of a body, wherein said first spinal prosthetic member comprises a first attachment member and a first articulating member that extends therefrom, and said second spinal prosthetic member comprises a second attachment member and a second articulating member that extends therefrom, said first articulating member articulating with said second articulating member, and wherein said first and second attachment members are attachable to spinal structure, and wherein said second articulating member has an inner hollow portion that fits over a protrusion that extends upward from said second attachment member, said protrusion together with said inner hollow portion of said second articulating member extending partially into a recess formed in said first articulating member along a second axis generally perpendicular to said lateral-medial axis so as to define a gap between an inner surface of said recess and an outer surface of said inner hollow portion along said second axis; and
a flexure limiting member attached to said first and second spinal prosthetic members, which limits flexure about the lateral-medial axis, wherein said flexure limiting member comprises an at least partial boot, and wherein articulation between said first articulating member and said second articulating member is restricted to be along an anterior face of one of the articulating members and a posterior face of the other articulating member.

2. Apparatus according to claim 1, wherein said boot is placed at least partially around said first and second articulating members.

3. Apparatus according to claim 1, wherein said flexure limiting member is constructed of at least one of polyurethane and polyetheretherketone.

4. Apparatus according to claim 1, wherein said first and second attachment members each comprise a plate with a prong that extends outwards therefrom generally parallel to said lateral-medial axis.

5. Apparatus according to claim 1, wherein said protrusion extends upward from a flat plate of said second attachment member.

6. Apparatus according to claim 1, wherein said second articulating member is constructed of a compliant, elastomeric material.

7. Apparatus according to claim 1, wherein said second articulating member has outer curved edges adjacent said protrusion.

8. Apparatus according to claim 1, wherein said flexure limiting member has at least one first curved portion and a second curved portion, curved opposite to the at least one first curved portion and joined thereto at an inflection point.

9. Apparatus according to claim 1, wherein said flexure limiting member comprising attachment elements that pass through and are resiliently held at mounting holes formed in said first and second attachment members.

10. Apparatus according to claim 1, wherein said flexure limiting member comprises one or more slim elongate members shaped as wires.

11. Apparatus according to claim 1, wherein said first articulating member articulates omnidirectionally with said second articulating member.

12. Apparatus according to claim 1, wherein said flexure limiting member is attached to a non-peripheral portion of said first and second attachment members.

13. Apparatus according to claim 1, wherein articulation between said first articulating member and said second articulating member is restricted to be along an anterior face of said first articulating members and a posterior face of said second articulating member.

14. Apparatus according to claim 1, wherein said second articulating member extends from said second attachment member more than halfway towards said first attachment member.

15. Apparatus according to claim 1, wherein said first articulating member extends from said first attachment member more than halfway towards said second attachment member.

* * * * *